United States Patent [19]

Flammer

[11] Patent Number: 4,863,261

[45] Date of Patent: Sep. 5, 1989

[54] METHOD OF AND APPARATUS FOR MEASURING THE EXTENT OF CLOUDING OF THE LENS OF A HUMAN EYE

[75] Inventor: Josef Flammer, Uettligen, Switzerland

[73] Assignee: Interzeag AG, Schlieren, Switzerland

[21] Appl. No.: 3,968

[22] Filed: Jan. 16, 1987

[30] Foreign Application Priority Data

Jan. 21, 1986 [CH] Switzerland .................... 217/86

[51] Int. Cl.⁴ ................................... A61B 3/10
[52] U.S. Cl. ................................ 351/221; 351/246
[58] Field of Search ............... 351/205, 221, 211, 213, 351/246; 356/346, 442

[56] References Cited

U.S. PATENT DOCUMENTS 3,600,094 8/1971 Liskowitz ........................ 356/342
4,662,731 5/1987 Robert et al. ................... 351/221

Primary Examiner—Rodney B. Bovernick
Assistant Examiner—J. P. Ryan
Attorney, Agent, or Firm—Peter K. Kontler

[57] ABSTRACT

The extent of clouding of the lens of a human eye is measured and quantified by directing a beam of electromagnetic radiation through the iris and against the clouded portion of the lens so that the clouded portion disperses and reflects the incident radiation. A selected part of reflected radiation which makes an angle of 10°–40° with the beam of incident radiation is monitored for intensity by a photoelectronic transducer whose signals are transmitted to an ammeter or to a microprocessor which latter transmits modified signals to a display unit and/or to a printer. The clouded portion of the lens can be observed through an optical system with an ocular whose axis coincides with a portion of the path of incident radiation.

18 Claims, 1 Drawing Sheet

METHOD OF AND APPARATUS FOR MEASURING THE EXTENT OF CLOUDING OF THE LENS OF A HUMAN EYE

BACKGROUND OF THE INVENTION

The invention relates to a method of and to an apparatus for determining the extent of clouding of the lens of a human eye.

It is already known to quantify the perimetrically determinable damages to the field of view, and such quantification again confirms the development of more or less diffuse damages in the event of glaucoma. The indices MD (mean defect), CLV (corrected loss variance) and SF (short term fluctuation) define the field of view with reference to the main axis whereby the index MD denotes the diffusion-causing damage to the eye.

The diffusion-causing damage is attributable to glaucoma and/or to a cataract. It is important that the physician in charge ascertain the actual cause of an increased or intensified mean defect, i.e., that the physician ascertain the percentage of diffusion-causing damage which is attributable to a cataract rather than to glaucoma.

Furthermore, heretofore known methods and apparatus for inspection and testing of human eyes cannot furnish any quantitative information pertaining to clouding of the lens. Thus, the physicians are compelled to define the clouding in ambiguous terms such as "slight clouding", "medium clouding" and the like.

OBJECTS AND SUMMARY OF THE INVENTION

An object of the invention is to provide a novel and improved method of quantifying the extent of clouding of the lens of a human eye with a heretofore unmatched degree of accuracy so that the heretofore necessary subjective quantification can be replaced with a measurement which furnishes information regarding that percentage of the mean defect which is caused by a cataract.

Another object of the invention is to provide a novel and improved apparatus for the practice of the above outlined method.

A further object of the invention is to provide novel and improved means for processing signals which are generated by a clouded portion of the lens of a human eye.

An additional object of the invention is to provide an apparatus which is simple, compact and relatively inexpensive, and which can be designed to display the information pertaining to the differential cross section of the beam of radiation that is reflected and dispersed by the clouded portion of the lens.

One feature of the present invention resides in the provision of a method of measuring the extent of clouding of the lens of a human eye, comprising the steps of directing at least one beam of electromagnetic radiation along a first path through the iris and into the lens of the eye so that the clouded portion, if any, of the lens disperses the incident radiation and a portion of dispersed radiation is reflected by the clouded portion of the lens along a second path, monitoring in said second path at least one characteristic of reflected radiation which is indicative of the extent of dispersion (differential cross section) of incident radiation and hence of the extent of clouding of the radiation-reflecting portion of the lens, generating signals which are indicative of the monitored characteristic, and processing the signals, (e.g., by feeding them to an alphanumerical display unit, to a printer and/or to an amperemeter or another instrument. For example, the processing step can include the step of averaging the intensity of the signals.

The electromagnetic radiation can be furnished by a light source, e.g., a source of monochromatic, polarized and/or coherent light.

The method can further comprise the step of modulating the beam of radiation in the first path; such modulating step can include pulsating the beam.

The first and second paths preferably make an angle which is less than or does not appreciably exceed 90°. In accordance with a presently preferred embodiment of the method, the angle is between 10 and 40°.

Another feature of the invention resides in the provision of an apparatus for measuring the extent of clouding of the lens of a human eye. The apparatus comprises a source of electromagnetic radiation including means for directing at least one beam of radiation along a first path through the iris and into the lens of the eye of a patient so that the clouded portion (if any) of the lens disperses the incident radiation and a portion of dispersed radiation is reflected by the clouded portion of the lens along a second path which is inclined with reference to the first path. The apparatus further comprises means for monitoring in the second path at least one characteristic (e.g., intensity) of reflected radiation which is indicative of the extent of dispersion (differential cross section) of incident radiation (and hence of the extent of clouding of the lens), including means (e.g., an optoelectronic transducer) for generating signals which are indicative of the monitored characteristic. The first and second paths preferably make an angle of less than 91°, most preferably an angle of 10°–40°.

The source of electromagnetic radiation can include a source of light, and the apparatus can further comprise means for modulating (e.g., pulsating) the beam of radiation which issues from the source. In accordance with a presently preferred embodiment of the apparatus, the source includes a slit lamp having an ocular the optical axis of which coincides with the second path. The signal generating means of such apparatus can include photoelectronic transducer means disposed in the second path behind the ocular.

The apparatus can further comprise means for permitting observation of the lens, including an optical system whose axis coincides with at least a portion of the first path. The optical system can comprise a conventional ocular.

The apparatus can further comprise means for processing the signals, and such processing means can include means for displaying the processed signals, e.g., by transmitting such signals to a screen or to other suitable displaying means, or to a printer which displays the modified signals on a tape, a paper strip or the like.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
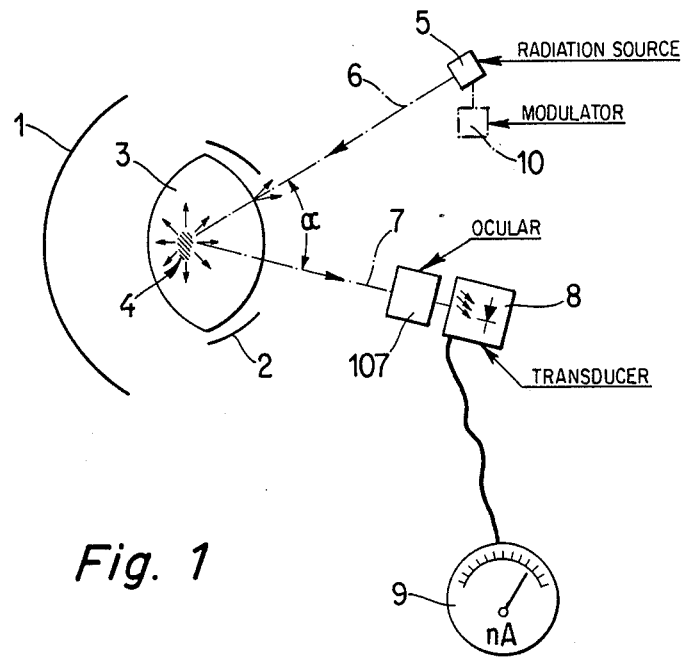
FIG. 1 is a schematic view of an apparatus which embodies the invention and wherein signals denoting the intensity of reflected radiation are transmitted to a nanoamperemeter.

FIG. 1 shows the retina 1, the iris 2 and the lens 3 of a human eye. The lens 3 has a clouded portion 4 which is or can be attributable to the age of the patient or to a disease (cataract). The clouded portion 4 is assumed to be of such nature that it adversely affects the effectiveness of the eye even if the retina 1 is intact.

The apparatus for measuring the extent of clouding or obscuring of the lens 3 comprises a radiation source 5 which emits a beam of radiation along a first path 6 extending through the diaphragm of the iris 2 and impinging upon the clouded portion 4. The latter disperses and reflects the incident beam of radiation and some of the dispersed and reflected radiation propagates itself along a second path 7 which is inclined with reference to the first path 6. The extent to which the clouded portion 4 disperses the beam which impinges upon it after having advanced along the path 6 is proportional to the cloudiness of the lens 3, i.e., the diffusion of incident radiation is more pronounced if the clouded portion 4 is more pronounced.

The improved apparatus further comprises means for monitoring the reflected radiation, and such monitoring means includes a photoelectronic transducer 8 which is installed in the second path 7 and generates signals denoting at least one characteristic of the reflected light, namely a characteristic which is indicative of the degree of dispersion of incident radiation by the clouded portion 4. The signals which are transmitted by the transducer 8 form a photocurrent which is supplied to a simple signal processing device in the form of a nanoamperemeter 9 with a pointer and a suitably calibrated scale to indicate the seriousness of the clouding of the lens 3 in appropriate units.

Figure 2:
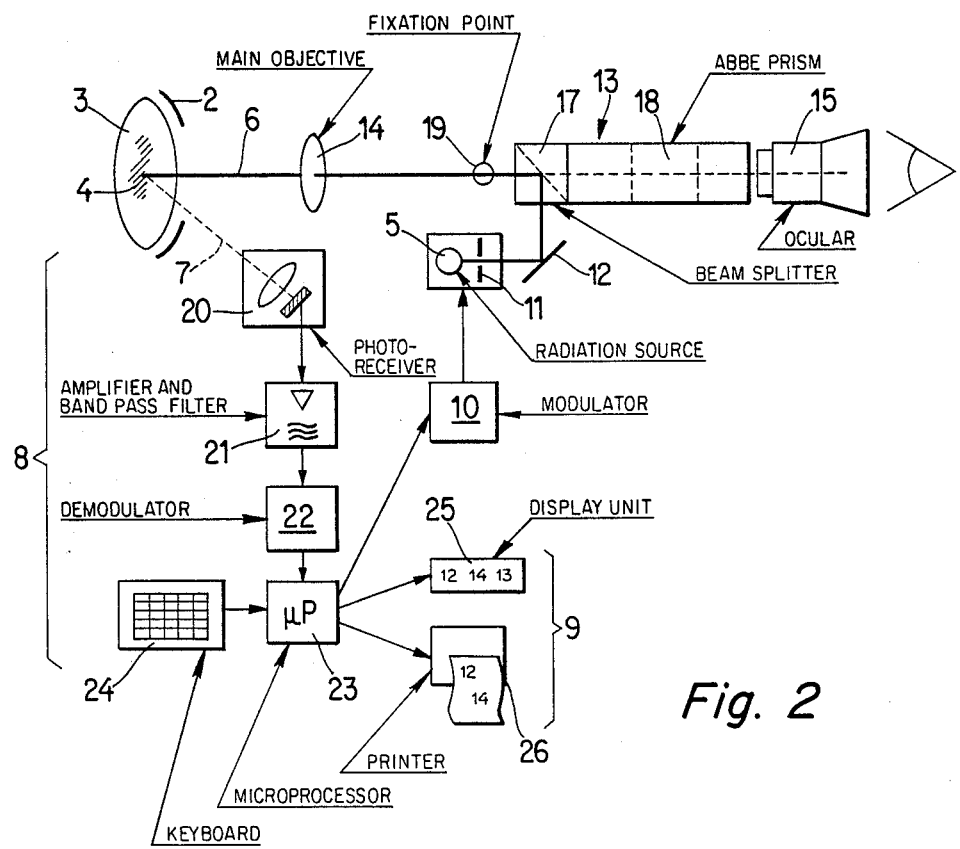
FIG. 2 is a diagrammatic view of a second apparatus wherein signals which denote the intensity of reflected radiation are processed by a computer and are transmitted to a display unit as well as to a printer.

The apparatus of FIG. 1 further comprises (or can further comprise) a host of additional components including mirrors which direct radiation along selected paths, filters and/or other optical elements. Some of these optical elements are shown in FIG. 2. The radiation source 5 is or can be selected in such a way that it emits monochromatic light. FIG. 1 further shows a modulator 10 which can influence the beam of radiation in the path 6, e.g., to modulate the intensity of radiation which is being emitted by the source 5 toward the iris 2. For example, the radiation source 5 can emit a bundle of light which is used as an orientation beam and the modulator 10 can periodically increase the intensity of emitted light in pulsating fashion. The source 5 can emit radiation in the infrared or in the ultraviolet range of the spectrum or in the visible light range. The angle alpha between the paths 6 and 7 is preferably less than 91°, more preferably between 5 and 90° and most preferably between 10 and 40°.

The radiation source 5 can constitute the light source of a slit lamp which includes means (such as binoculars) for permitting observation of the clouded portion 4 along the second path 7. To this end, the slit lamp includes an ocular 107 whose axis coincides with the path 7.

A portion of radiation which is reflected by the clouded portion 4 of the lens 3 into and propagates itself along the path 7 can be deflected between the observation objective and one of the two oculars of the slit lamp by a partially transmitting mirror to impinge upon the photoelectronic transducer 8. It is equally within the purview of the invention to replace one ocular of the slit lamp with a light measuring head which includes the transducer 8. It is presently preferred to employ a transducer 8 wherein the spectral sensitivity distribution is the same as that of the human eye and to place the transducer behind a suitable filter. This ensures that the quantification of cloudiness of the lens corresponds to the subjective sensation of the patient.

The photoelectronic transducer 8 can be replaced with a video camera whose images are electronically stored in a suitable memory. The camera can be used in conjunction with a computer which processes the signals from the camera and displays them in the form of curves, or which integrates or otherwise averages the signals and transmits a single averaged signal.

The nanoamperemeter 9 of FIG. 1 can be replaced with a more sophisticated (e.g., electronically controlled) signal receiving and processing device of any known design.

FIG. 2 shows a modified apparatus wherein all such parts which are identical with or clearly analogous to corresponding parts of the apparatus of FIG. 1 are denoted by similar reference characters. The radiation source 5 comprises a light emitting diode which is designed to emit light in the dark red range (approximately 690 nm). The light beam transfer from the source 5 through an adjustable diaphragm 11 and is deflected by a mirror 12 to impinge upon a partially light transmitting prismatic beam splitter 17. The thus deflected beam of radiation passes through the main objective 14 of an optical system 13 whose axis coincides with the first path portion extending to the clouded portion 4 of the lens 3 behind the iris 2 of the eye of the patient. The diaphragm 11 can be set to permit the passage of a beam having a diameter of 1.3–3 mm. If desired, the aperture of the diaphragm 11 can have a noncircular outline in order to reduce the likelihood of excessive reflection of the beam of incident radiation by the cornea of the eye of the patient.

The main objective 14 serves to image the iris 2 in the ocular 15 of the optical system 13 (e.g., a suitable telescope), and to image the beam of red light which is directed toward the iris 2 along the path 6. The beam splitter 17 of the optical system 13 mixes the radiation in the respective portion of the path 6. An Abbe prism 18 of the optical system 13 is disposed between the beam splitter 17 and the ocular 15 to reverse the image. A fixation point 19 is provided in the first path to enable the patient to look in the direction toward the beam splitter 17.

The clouded portion 4 can constitute a cataract which disperses and reflects some of the incident radiation into the path 7 wherein the reflected radiation impinges upon the photoreceiver 20 of a transducer 8. The receiver 20 can include an optical element and a preamplifier which directs signals to a second component 21 of the transducer 8, preferably a combined amplifier and band pass filter whose output is connected with a demodulator 22 having an output connected with the corresponding input of a microprocessor 23. The band pass filter of the component 21 eliminates or reduces the influence of undesirable factors, and the amplifier of the component 21 intensifies the signals to a level which is required for convenient processing in the microcomputer 23. The demodulator 22 serves to relieve the signals of noise and to demodulate the signals so that they are devoid of radiation which is attributable to daylight or artificial light, i.e., the signals which reach the microcomputer 23 are derived solely from radiation which is emitted by the source 5. An analog-digital converter (not specifically shown) is installed between the demodulator 22 and the microprocessor 23 which latter is equipped with a keyboard 24. The microprocessor 23 of the transducer 8 processes the digital signals in accordance with selected mathematical algorithms before the signals reach an alphanumerical display unit 25. If desired, the output of the microcomputer 23 can be connected with the input of a printer 26 which can be used with or in lieu of the display unit 25. The components 25, 26 together constitute a functional equivalent of the amperemeter 9 of FIG. 1.

An output of the microcomputer 23 is connected with the modulator 10 for the beam of radiation issuing from the source 5.

The apparatus of the present invention can be designed to measure the polarization of light which is attributable to the presence of a cataract 4. Such polarization measurement (in the path 7) can take place in addition to or in lieu of a measurement of intensity of reflected radiation. This is often desirable and advantageous if the source 5 emits nonpolarized light.

The monitoring means (transducer 8) can further comprise means for monitoring the electric or magnetic field of radiation in the path 7 to ascertain the energy density which is directly proportional to the rate of dispersion of radiation by the cataract 4. If the source 5 emits monochromatic light, the monitoring means can operate in accordance with fresnel interference principles to ascertain the extent to which the dispersion of light affects the monochromaticity of light (nonelastic dispersion) which is an indication of the rate of dispersion of light by the cataract 4.

Slit lamps which can be used in the apparatus of the present invention are manufactured and sold by Haag-Streit AG, Hess-Str. 27, CH-3097 Liebefeld, Switzerland.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of measuring the extent of clouding of the lens of a human eye, comprising the steps of directing at least one beam of electromagnetic radiation along a first path through the iris and into the lens of the eye so that the clouded portion, if any, of the lens disperses the incident radiation and a portion of dispersed radiation is reflected by the clouded portion of the lens along a second path; monitoring in said second path the extent of dispersion of incident radiation and generating signals which are indicative of the dispersion; and processing said signals.

2. The method of claim 1, wherein said signals vary and said processing step includes averaging the magnitudes of said signals.

3. The method of claim 1, wherein the electromagnetic radiation is light.

4. The method of claim 3, wherein the light is monochromatic light.

5. The method of claim 3, wherein the light is polarized light.

6. The method of claim 3, wherein the light is coherent light.

7. The method of claim 1, further comprising the step of modulating the beam of radiation in said first path.

8. The method of claim 7, wherein said modulating step includes pulsating the beam of radiation in said first path.

9. The method of claim 1, wherein the first and second paths make an angle of less than 91°.

10. The method of claim 9, wherein said angle is between 10 and 40°.

11. Apparatus for measuring the extent of clouding of the lens of a human eye, comprising a source of electromagnetic radiation including means for directing at least one beam of radiation along a first path through the iris and into the lens of the eye so that the clouded portion, if any, of the lens disperses the incident radiation and a portion of dispersed radiation is reflected by the clouded portion of the lens along a second path which is inclined with reference to said first path at an angle of between 10° and 40°; and means for monitoring the extent of dispersion of incident radiation, including means for generating signals which are indicative of the dispersion.

12. The apparatus of claim 11, wherein said source includes a source of light.

13. The apparatus of claim 11, further comprising means for modulating the beam of radiation in said first path.

14. The apparatus of claim 13, wherein said modulating means comprises means for pulsating the beam of radiation in said first path.

15. The apparatus of claim 11, further comprising means for permitting observation of the lens including an optical system having an axis coinciding with at least a portion of least said first path.

16. The apparatus of claim 15, wherein said optical system includes an ocular.

17. The apparatus of claim 11, further comprising means for processing said signals and means for displaying the processed signals.

18. Apparatus for measuring the extent of clouding of the lens of a human eye, comprising a source of electromagnetic radiation including means for directing at least one beam of radiation along a first path through the iris and into the lens of the eye so that the clouded portion, if any, of the lens disperses the incident radiation and a portion of dispersed radiation is reflected by the clouded portion of the lens along a second path which is inclined with reference to said first path, said source including a slit lamp having an ocular with an optical axis coinciding with said second path; and means for monitoring in the second path the extent of dispersion of incident radiation, including means for generating signals which are indicative of dispersion, said signal generating means including photoelectronic transducer means disposed in said second path downstream of said ocular.

* * * * *